(12) United States Patent
Woo et al.

(10) Patent No.: US 8,822,705 B2
(45) Date of Patent: Sep. 2, 2014

(54) PHARMACEUTICAL COMPOSITION FOR PREVENTING AND/OR TREATING BONE DISEASE, FUNCTIONAL FOOD OR HEALTH FOOD AND PHARMACEUTICAL PREPARATION COMPRISING THEREOF AS ACTIVE INGREDIENT

(75) Inventors: Je-Tae Woo, Tokyo (JP); Masato Ohta, Chiba (JP); Takayuki Yonezama, Aichi (JP); Toshiaki Teruya, Kanagawa (JP); Byung-Yoon Cha, Aichi (JP); Kazuo Nagai, Tokyo (JP); Toshihiro Akihisa, Tokyo (JP); Hiroyuki Akazawa, Tokyo (JP)

(73) Assignees: Toshihiro Akihisa, Tokyo (JP); Kazuo Nagai, Tokyo (JP)

( * ) Notice: Subject to any disclaimer, the term of this patent is extended or adjusted under 35 U.S.C. 154(b) by 103 days.

(21) Appl. No.: 12/362,938

(22) Filed: Jan. 30, 2009

(65) Prior Publication Data

US 2009/0227527 A1    Sep. 10, 2009

Related U.S. Application Data

(63) Continuation of application No. PCT/JP2007/065160, filed on Aug. 2, 2007.

(30) Foreign Application Priority Data

Aug. 2, 2006 (JP) .................................. 2006-211385

(51) Int. Cl.
  *C07H 15/24*     (2006.01)
  *C07H 15/26*     (2006.01)
  *A61K 31/7048*   (2006.01)
  *A61K 31/335*    (2006.01)
  *C07D 313/00*    (2006.01)

(52) U.S. Cl.
  CPC .............. *C07D 313/00* (2013.01); *C07H 15/24* (2013.01); *C07H 15/26* (2013.01); *A61K 31/7048* (2013.01); *A61K 31/335* (2013.01)
  USPC ........................................... 549/200; 536/7.1

(58) Field of Classification Search
  None
  See application file for complete search history.

(56) References Cited

U.S. PATENT DOCUMENTS

2004/0091544 A1* 5/2004 Ruff et al. ....................... 424/490
2005/0215635 A1  9/2005 Rafi et al. ....................... 514/546

FOREIGN PATENT DOCUMENTS

JP    2001-226263 A1   8/2001
JP    2006-137679 A1   6/2006

OTHER PUBLICATIONS

The Merck Mantual of Diagnosis and Therapy, published 1999 by Merck Research Laboratories, pp. 35-39, 407, 408, and 2409-2414.*
Akihisa et al., "Acerogenin M, a Cyclic Diarylheptanoid, and Other Phenolic Compounds from Acer nikoense and Their Anti-inflammatory and Anti-tumor-Promoting Effects" Chemical and Phermaceutical Bulletin (2006) vol. 54 No. 5, pp. 735-739.*
Merriam-Webster's Collegiate Dictionary, Tenth Edition, published 1998 by Merriam-Webster, Incorporated, p. 924.*
Yin, J., et al, "New Diarylheptanoids from the Rhizomes of *Dioscorea spongiosa* and Their Antiosteoporotic Activity," Planta Med., vol. 70, 2004, pp. 54-58.
Supplementary European Search Report dated Mar. 17, 2010.
T. Yonezawa, et al.; "Effects of diarylheptanoid compounds derived from a bark of Megusurinoki to osteoblast differentiation;" Abstract for Annual Meeting of Japan Pharmaceutical Society of Japan; vol. 127; No. 2; Mar. 2007; p. 144 at the bottom right [28P2-pm071] (1 Sheet.).
M. Shinoda, et al.; "Protective Effect of the Bark of Acer nikoense on Hepatic Injury Induced by Carbon Tetrachloride in Rats;" The Japanese Journal of Pharmacognosy; vol. 40; No. 2; 1986; pp. 177-181 (5 Sheets.).
J. Ishida, et al.; Antitumor Agents. Part 214: Synthesis and Evaluation of Curcumin Analogues as Cytotoxic Agents; Bioorganic & Medicinal Chemistry; vol. 10; 2002; pp. 3481-3487 (7 Sheets.).
International Search Report for International Application No. PCT/JP2007/065160 dated Sep. 13, 2007.
Nagumo, Seiji et al., "Studies on the Constituents of Aceraceae Plants. XI. Two Types of Cyclic Diarylheptanoid from *Acer nikoense*", Chemical & Pharmaceutical Bulletin, Pharmaceutical Society of Japan, vol. 41, No. 7, Jul. 1, 1993, pp. 1255-1257.

(Continued)

*Primary Examiner* — Eric S Olson
(74) *Attorney, Agent, or Firm* — Kratz, Quintos & Hanson, LLP

(57) ABSTRACT

The present invention provides a highly safe pharmaceutical composition for preventing and/or treating bone disease, a pharmaceutical preparation comprising thereof, a health food comprising thereof, a functional food comprising thereof. Since the present invention comprises the arylheptanoid compound shown in the following formula (I) and the derivatives thereof, it enables to prevent and/or treat the bone disease.

(In the formula (I), $R^1$ and $R^5$ are a functional group selected from the group consisting of a hydrogen atom, alkyl group having carbon numbers 1 to 3, monosaccharide and disaccharide; $R^2$, $R^3$, and $R^4$ are a functional group selected from the group consisting of a hydrogen atom, an oxygen atom, alkyl group having carbon numbers 1 to 3, monosaccharide and disaccharide; $R^5$ may be bound on meta-position against heptylene group of another aryl group to form a ring.)

5 Claims, 6 Drawing Sheets
(2 of 6 Drawing Sheet(s) Filed in Color)

(56) References Cited

OTHER PUBLICATIONS

Nagai, Masahiro et al., "Studies on the Constituents of Aceraceae Plants. VI. Revised Stereochemistry of (−)-Centrolobol, and New Glycosides from *Acer nikoense*", *Chemical & Pharmaceutical Bulletin, Pharmaceutical Society of Japan*, vol. 34, No. 3, Jan. 1, 1986, pp. 1056-1060.

Morikawa, Toshio et al., "Structures of New Cyclic Diarylheptanoids and Inhibitors of Nitric Oxide Production from Japanese Folk Medicine *Acer nikoense*", *Journal of Natural Products*, vol. 66, 2003, pp. 86-91.

European Search Report dated Dec. 8, 2011, in counterpart European Application No. 11184774.5.

Indian Office Action dated Mar. 5, 2014, in the corresponding Indian patent application No. 255/MUMNP/2009.

Korean Office Action dated Jan. 28, 2014, in the corresponding Korean Application No. 10-2009-7002248, with English translation.

* cited by examiner acerogenin A (R)-acerogenin B

Alizarin Red S Staining

PBS acerogenin A

PHARMACEUTICAL COMPOSITION FOR PREVENTING AND/OR TREATING BONE DISEASE, FUNCTIONAL FOOD OR HEALTH FOOD AND PHARMACEUTICAL PREPARATION COMPRISING THEREOF AS ACTIVE INGREDIENT

RELATED APPLICATION

This is a continuation application of the international patent application No. PCT/JP2007/065160 filed with Application date: Aug. 2, 2007. The present application is based on, and claims priority from, J.P. Application 2006-211385, filed on Aug. 2, 2006, the disclosure of which is hereby incorporated by reference herein its entirety.

BACKGROUND OF THE INVENTION

The present invention relate to an application way of extracts from plants containing a compounds shown in a following formula (I) and derivatives thereof, diarylheptanoid compounds and their derivatives, obtained from crude drug components.

[Chemical formula 1]

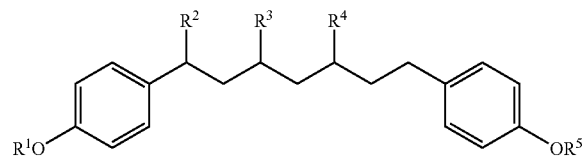

(I)

(In the formula (I), $R^1$ is a functional group selected from the group consisting of a hydrogen atom, alkyl group having carbon numbers 1 to 3, monosaccharide and disaccharide; $R^2$, $R^3$ and $R^4$ are the functional group selected from the group consisting of a hydrogen atom, hydroxyl group, the alkyl group having carbon numbers 1 to 3, monosaccharide and disaccharide; $R^5$ is a hydrogen atom, the alkyl group having carbon numbers 1 to 3, monosaccharide and disaccharide, or it may be bound on meta-position against heptylene group bound on another aryl group to form a ring. Each aryl group may be respectively bound between carbons located in meta-position against the heptylene group to form a ring.)

More specifically, the present invention relates to a functional food, a health food, a pharmaceutical composition for preventing and/or treating bone disease comprising at least one of diarylheptanoid compounds shown in the above-mentioned chemical formula (I) or derivatives of them, and a pharmaceutical preparation comprising the composition as an active ingredient. In the present specification, the term "derivatives" contains physiologically acceptable salts and hydrates of the compounds shown in the chemical formula (I).

BACKGROUND ART

Bone-relating disease to bone are classified into an exogenous disease represented by traumatic bone fracture or stress fracture, and an endogenous disease represented by pre-osteoporosis, osteoporosis, hypercalcemia, hyperparathyroidism which excrete parathyroid hormone (referred to as "PTH" herein below), Paget disease, arthritis rheumatism, bone metastasis of breast cancer, osteomalacemia, fragility of osseous tissue caused by the disease such as malignant tumor or malnutrition. In the specification, the term "bone-related disease" includes also resorption of alveolar bone and diseases caused by the resorption addition to the exogenous disease and endogenous diseases.

In human bones, homeostasis is maintained by repeating osteogenesis performed by osteoblasts and bone resorption performed by osteoclasts continuously. However, if homeostasis is not maintained caused by ageing or inflammation to generate over bone resorption, clinical conditions such as osteoporosis, rheumatoid arthritis and so forth appear.

Among the endogenous diseases, numbers of osteoporosis patients are growing correlating to the number of growing population of aged people. Also, it is said that amounts of calcium intake or fixation ratio of calcium to osseous tissue is decreased because of changed diet and decreased amount of exercise promote the fragilitization of osseous tissue.

The bone fracture is defined as the situation in which a part of the connection between osseous tissues is broken by external force, accompanying with apparent pain on the fractured site. The bone is not fractured in a healthy person, unless it is subjected to further high external force, for example, caused by a traffic accident. However, the osseous tissue is weakened caused by loosing bone mass, the bone is fractured when it is subjected to modest or low external force caused by falling during walking or running. Alternatively, the bone mass is lost caused by the endogenous disease such as the osteoporosis described above end so forth, the bone will be fractured when it is subjected to very low external force caused by stumbling on the stairs, or coughing.

In general, when the bone is fractured, the treatment method such that the sites of the bone is corrected to right position by undergoing traction treatment, and to be fixed the fractured bones by using pins or bolts if possible, depending on natural healing ability.

When a teeth is lose by affecting periodontitis, an alveolar bone, which is also that of upper or lower jaw and supports teeth, of the teeth were lost is resorbed so that it leads that other tooth are not well supported. In general, loosing the teeth causes to resorb the alveolar bone around the teeth, because of the necessity for supporting the teeth by the alveolar bone is lost; other tooth become easily lost. Then, the person can not intake nutrition necessary for the bone formation by taking insufficient meals, and off balance between the bone formation and the bone resorption leads development of the endogenous bone disease such as osteoporosis and the like.

On the other hand, the endogenous disease such as osteoporosis generates the both loss of calcareous in the bone and bone matrix so that it often makes the natural healing delay. As a result, ankylosis is generated articulations other than the fractured site in the case of the aged people, and it often makes the people an invalid.

Accordingly, when the treatment of the bone fracture, particularly in the aged people, is performed, there are strong social needs to shorten the time period for the treatment, from the viewpoint of decreasing the number of the people who require nursing care. On the other hand, there are other needs for the safety of the pharmaceutical preparations used in the treatment such as fewer side effects.

In the treatment for the bone disease, conventionally, activated vitamin $D_3$ which is a vitamin D derivative that plays an important role in calcium metabolism, calcitonin and its derivatives, the hormone preparations such as estradiol and so forth, as well as a variety of calcium preparations have been used in the treatment for the bone disease.

However, there is a problem that several preparations can not be administrated per os depending on their absorption into a body or metabolism in a body; or their effects are not predictable because of individual variety of receptor level. Therefore, a new treatment preparation that is an alternative to them is required.

On the other hand, conventionally, leaves, whole parts of grasses, roots, and fruits of plants which have been used as Japanese or Chinese crude drugs or herb teas (hereinbelow, they are referred to as "crude drugs"). Analysis of them demonstrated that they comprise a variety of compounds, and also it is demonstrated gradually that they have different effects except these known in conventionally.

For example, since a bark of Megusurinoki (Acer nikoense, of which another name is a "millionaire tree") was infused to be used as an eye wash by in convention, it was given the name "Megusurinoki", a tree of eye-drops), and it is also effective to asthenopia or liver. Furthermore, recently it is reported that extracts from its bark has a melanin syntase inhibition effect (see Patent reference 1), anticancer effect (see Patent reference 3 and 4), and the like.

In order to prevent the situation for loosing tooth caused by resorption of the alveolar bone or improve the condition of the alveolar bone, GTR (Guided Tissue Regeneration) method and EMDOGAIN (registered trade mark) method have been developed. GTR method has been developed in the middle of 1980s, and a membrane made of Gore-Tex for medical application is placed in a space formed by bone resorption so as to regenerate the bone. In the method, the membrane was inserted under gingiva gently and then stura of the gingiva should be performed. Since Asian people have thin gingiva compared to Westerner, surgical operation becomes complicated and the membrane is sometimes exposed from the gingiva several days after the surgical operation. If this could occur, a patient has episode of infection so that the alveolar bone is not formed.

EMDOGAIN (registered trademark) is the pharmaceutical preparation by using a biological material for resolving such problems. The preparation employs protein extracted from tooth germ of a juvenile swine to attract the bone around the teeth to regenerate by setting the same environment as cutting a tooth.

The preparation is effective when the bone is partially resorbed, namely one mural vertical bone defect. However, it can not be applied when the bone around the teeth entirely, 360 degree, has been defected. Furthermore, since the preparation is made of the biological material, there is no guarantee that anything would not be happen in future.

Patent reference 1: JP2006-137679A

Non-patent reference 1: T. Morikawa, J. Tao, K. Ueda, H. Matsuda and M. Yoshikawa, Medicinal Foodstuffs. XXXI. Structure of New Aromatic Constituents and Inhibitors of Degranulation in RBL-2H3 Cells from a Japanese Folk Medicine, the Stem Bark of Acer nikoense., Chem. Pharm. Bull., 51(1), 62-67 (2003).

Non-patent reference 2: T. Morikawa, J. Tao, I. Toguchida, H. Matsuda and M. Yoshikawa, Structure of New Cyclicdiarylheptanoids and Inhibitors of Nitric Oxide Production from Japanese Folk Medicine Acer nikoense., J. Nat. Prod., 66, 86-91 (2003).

Non-patent reference 3: J. Ishida, M. Kozuka, H. Tokuda, H. Nishino, S. Nagumo, K. H. Lee and M. Nagai, Chemopreventive Potential of Cyclicdiarylheptanoids., Bioorg. Med. Chem., 10, 3361-3365 (2002).

Non-patent reference 4: S. Okabe, M. Suganuma, Y. Imayoshi, S. Taniguchi, T. Yoshida and H. Fujiki, New TNF-a Releasing Inhibitors, Geraniin and Corilagin, in Leaves of Acer nikoense, Megusurino-ki., Biol. Pharm. Bull., 24(10), 1145-1148 (2001).

Non-patent reference 5: "Material for regeneration of periodontal tissue using swine embryo tissue, Biological Material EMDOGAIN Gel" (a pamphlet reserved by YOSHIDA Dental Trade Distribution Co. and SEIKAGAKU CORPORATION) EMD5 (RM) June 2005)

By the way, the most effective means to decrease the number of bone disease patients is prevention of the bone disease. Namely, for the healthy people, preventing the loss of bone mass or bone density can be the effective means; and for the nonprogressors whose bone mass or bone density is reduced but not the symptom is not appeared (so-called would-be patients of the bone disease), inhibiting the loss of bone mass or bone density, increasing bone mass or bone density as high as possible can be the effective means.

More specifically, precautions are taken depending on the stage of the patient how close the appearance point such as administration of the prophylactic pharmaceutical preparation or functional foods intake.

As mentioned above, there is the strong social need for the workable preventing means for not only the patients appearing the symptom, but also the nonprogressors or healthy people not to become patients in the bone disease.

SUMMARY OF THE INVENTION

The present invention is completed under the above-mentioned situation. Namely, inventors of the present invention performed screening to find out compounds having osteogenesis promoting activity among the components contained in plants used as the crude drugs or the herb teas from ancient age mainly, considering for showing high pharmacological effect and safety. As a result, the inventors found that the known compounds have novel activities, which have not known, and completed the present invention.

Namely, the first aspect of the present invention is a pharmaceutical composition for preventing and/or treating bone disease comprising diarylheptanoid compounds shown as the following formula (I) and glycosides thereof as an active ingredient.

As a result for a variety of screenings, it was demonstrated that the compounds shown in the following formula (I) and the glycoside thereof among the diarylheptanoid compounds and their glycosides have new activities for promoting osteoblast differentiation and calcification.

[Chemical formula 2]

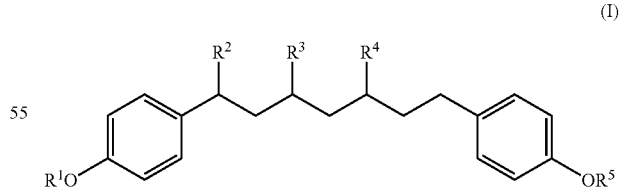

(I)

Wherein, $R^1$ is a functional group selected from the group consisting of a hydrogen atom, alkyl group having carbon numbers 1 to 3, monosaccharide and disaccharide; $R^2$, $R^3$ and $R^4$ are the functional group selected from the group consisting of a hydrogen atom, hydroxyl group, the alkyl group having carbon numbers 1 to 3, monosaccharide and disaccharide; $R^5$ is a hydrogen atom, the alkyl group having carbon numbers 1 to 3, monosaccharide and disaccharide, or it may bind on meta-position against heptylene group bound on another aryl group to form a ring. Each aryl group may be respectively bound between carbons located in meta-position against the heptylene group to form a ring.

The diarylheptanoid compound shown in the above-formula (I) is preferably that shown in the following formula (Ia), because it has the activities for promoting the systemic osteoblast differentiation and calcification.

[Chemical formula 3]

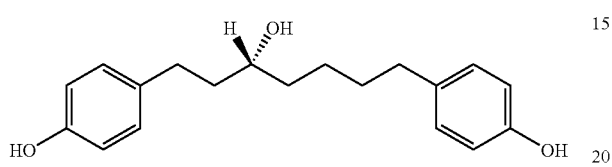
(Ia)

Furthermore, the diarylheptanoid compound shown in the above formula (I) and the glycoside thereof is preferably either compound shown in the following formulae (II) or (III).

[Chemical formula 4]

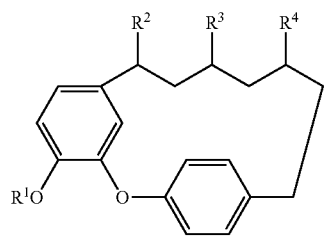
(II)

[Chemical formula 5]

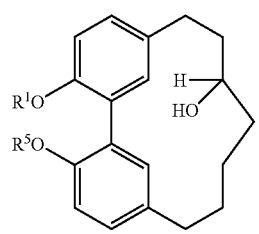
(III)

In the formulae (II) and (III), $R^1$ and $R^5$ are similar to those described above, the functional groups selected from the group consisting of a hydrogen atom, alkyl group having carbon numbers 1 to 3, the monosaccharide and the disaccharide; $R^2$, $R^3$ and $R^4$ are the functional group independently selected from the group consisting of a hydrogen atom, oxygen atom, hydroxyl group, the monosaccharide and the disaccharide Here, as the compounds shown in the formula (II) and the glycoside thereof, at least one compounds or glycoside selected from the group consisting of the compounds shown in the following formulae (IIa) to (IIh) and the glycoside thereof is preferable. The compound selected from the group consisting of these shown in the following formulae (IIa) to (IId) is more preferable, because they have high promotion activities of the osteoblast differentiation and calcification.

[Chemical formula 6]

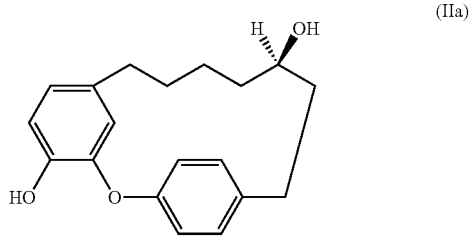
(IIa)

[Chemical formula 7]

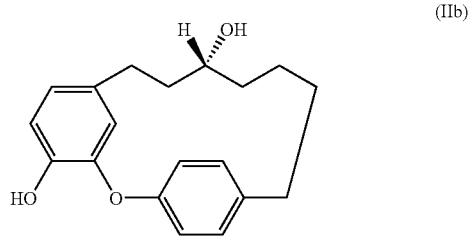
(IIb)

[Chemical formula 8]

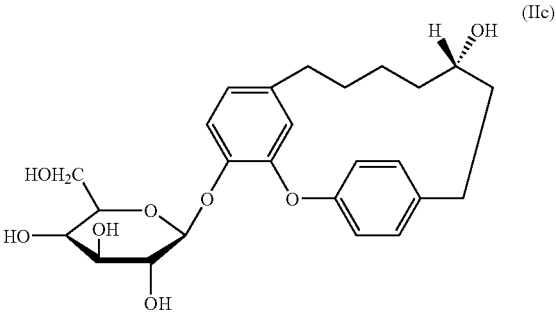
(IIc)

[Chemical formula 9]

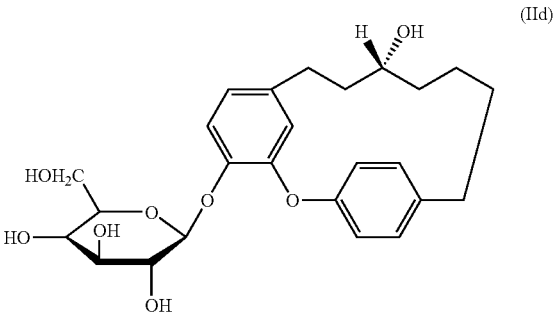
(IId)

[Chemical formula 10]

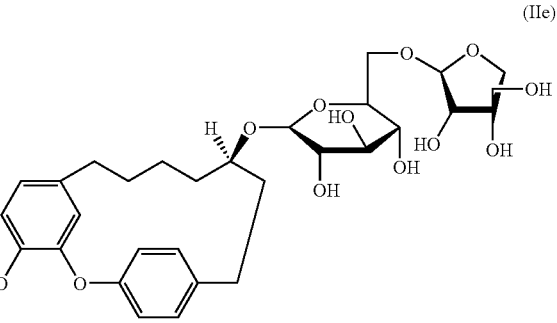
(IIe)

[Chemical formula 11]

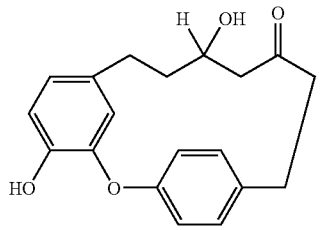
(IIf)

[Chemical formula 12]

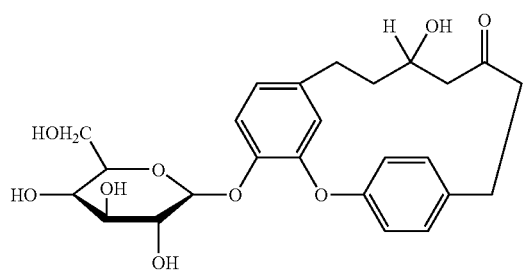
(IIg)

[Chemical formula 13]

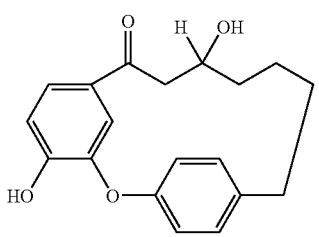
(IIh)

As the compound shown in the formula (III) and the glycoside thereof, being included in the pharmaceutical composition for preventing and/or treating bone disease as the active ingredient of the present invention, derivatives of the diarylheptanoid compound shown in the following formula (IIIa), physiologically acceptable salts thereof, or hydrates thereof are preferable.

[Chemical formula 14]

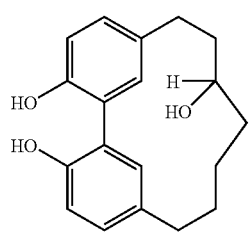
(IIIa)

Furthermore, as the compound being included in the pharmaceutical composition for preventing and/or treating bone disease as the active ingredient of the present invention, derivatives of the diarylheptanoid compound shown in the following formula (IV), the physiologically acceptable salts thereof, or hydrates thereof are preferable.

[Chemical formula 15]

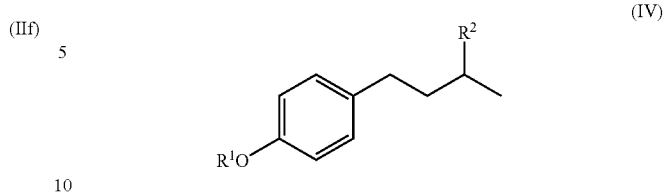
(IV)

In the formula (IV), $R^1$ is the functional group, similar to these described above, selected from the group consisting of a hydrogen atom, the alkyl group having carbon numbers 1 to 3, the monosaccharide and the disaccharide; $R^2$ is the functional group selected from the group consisting of a hydrogen atom, the hydroxyl group, the monosaccharide and the disaccharide.

Here, as the compound shown in the above formula (IV) and the glycoside thereof, being included in the pharmaceutical composition for preventing and/or treating bone disease as the active ingredient of the present invention, the derivatives of phenylbutanoid compound shown in the following formula (IVa), the physiologically acceptable salts thereof, or hydrates thereof are preferable.

[Chemical formula 16]

(IVa)

That is, the present invention is the pharmaceutical preparation comprising at least one selected from the group consisting of the above formulae (I), (II), (III), (IV) and glycoside thereof as the active ingredient, for preventing and/or treating bone disease.

Among these compounds and the glycoside thereof, the compounds shown in the above-mentioned formulae (Ia), (IIa) to (IIh), (IIIa) and (IVa) have these having the following names.

TABLE 1

| No. | Functional Groups | Compound Name |
| --- | --- | --- |
| Ia | $R^1$: H, $R^2$: H, $R^3$: OH, $R^4$: H, $R^5$: H | (−)-centrolobol |
| IIa | $R^1$: H, $R^2$: H, $R^3$: H, $R^4$: OH, $R^5$: none | acerogenin A |
| IIb | $R^1$: H, $R^2$: H, $R^3$: OH, $R^4$: H, $R^5$: none | (R)-acerogenin B |
| IIc | $R^1$: Glc*[1], $R^2$: H, $R^3$: H, $R^4$: OH, $R^5$: none | aceroside I |
| IId | $R^1$: Glc*[1], $R^2$: H, $R^3$: OH, $R^4$: H, $R^5$: none | aceroside $B_1$ |
| IIe | $R^1$: H, $R^2$: H, $R^3$: H, $R^4$: O-Glc*[1]-Api*[2], $R^5$: none | aceroside III |
| IIf | $R^1$: H, $R^2$: H, $R^3$: OH, $R^4$: =O, $R^5$: none | aceroside D |
| IIg | $R^1$: Glc, $R^2$: H, $R^3$: OH, $R^4$: =O, $R^5$: none | aceroside IV |
| IIh | $R^1$: H, $R^2$: =O, $R^3$: OH, $R^4$: H, $R^5$: none | aceroside M |
| IIIa | $R^1$: H, $R^5$: H | acerogenin K |
| IV | — | (+)-rhododendrol |

*[1] glucose
*[2] apiose

Among the compounds shown in the formulae (Ia), (IIa) to (IIh), (IIIa) and (IVa), the compound selected from the group consisting of aceroside I: (α-D-Glucopyranoside, (12S)-12-hydroxy-2-oxatricyclo[13.2.2.1$^{3,7}$]eicosa-3,5,7(20),15,17,18-hexaen-4-yl (9CI)), aceroside $B_1$ (α-D-Glucopyranoside, (10R)-10-hydroxy-2-oxatricyclo[13.2.2.1$^{3,7}$]eicosa-3,5,7 (20),15,17,18-hexaen-4-yl (9CI)), acerogenin A (2-Oxatricyclo[13.2.2.1$^{3,7}$]eicosa-3,5,7 (20),15,17,18-hexaene-4,12-diol, (12R)-(9CI)) and (R)-acerogenin B (2-Oxatricyclo[13.2.2.1$^{3,7}$]eicosa-3,5,7(20),15,17,18-hexaene-4,10-diol, (10R)-(9CI)) may be preferably used, because they have high promotion activities of osteoblast differentiation and calcification of the osteoblasts.

Hereinbelow, the compounds shown in the above-mentioned formulae (IIa) to (IIh) including the glycosides thereof are sometimes referred to as the "acerogenin and the like". These compounds and glycosides may be used as the physiologically acceptable salts thereof or hydrates thereof, depending on the needs. When the salt is used, it gives a merit the health food, the functional food, or the pharmaceutical preparations are easily prepared.

The compound shown in the formulae (Ia), (IIa) to (IIh), (IIIa) and (IVa) may be obtained from extracts from the dried bark of the trees selected from the group Megusurinoki (*Acer nikoense* Maximowicz), Sanfachi (Japanese name: Onimegusuri, *Acer triflorum*), Shuepichi (*Acer griseum*), Dakekannba (*Betula ermanii* Cham.), Shirakannba (*Betula platyphylla*), Udaikannba (*Betula maximowicziana*), Yaegawakannba (Koonoore, *Betula davurica* Pall.), Hannoki (*Alnus japonica* Steud.), and *Boswellia ovalifoliolata*).

Megusurinoki has another name, millionaire tree, and is naturally grown in a mountain area of Honshu and Shikoku island, as well as Kyushu Island except Miyazaki and Kagoshima prefectures. It belongs to Aceraceae indigenous to Japan, and is dioecism. Since grey color bark of the tree is taken and dried, and then infused to prepare the eye lotion, it is called as "Megusurinoki".

Megusurinoki has a long history, and at the age of provincial wars, it has become widely popular that it is sovereign remedy for diseases of eyes around Kitaohmi or Banshu. In leaves of the tree, β-amylin as triterpenoid, β-sitosterol glycoside as sterols, quercetin or its glycosides as flavonol, ellagic acid as a derivative of benzoic acid, geraniin as tannin, and the like are included.

In the trunk of the tree, the β-sitosterol and its glycosides, scoporetin as coumarin, aceroside I as the glycoside, epi-rhododendrin, and so forth are included.

Furthermore, in the bark of the trees, β-amylin, β-sitosterol and its glycosides included also in the leaves, scoporetin, methyl hematommate, rhododendrol, acerogenin, catechin, epi-rhododendrin, and the like are included.

From the trunk barks of Sanfachi (Onimegusuri, *Acer triflorum*) originated from Northern China and Korea, and Shuepichi (*Acer griseum*) originated from Sichuan and Hubei in China, aceroside IX and aceroside X are obtained. Acid hydrolysis of aceroside IX gives acerogenin G, and sugars such as glucose and apiose.

All of Dakekannba (*Betula ermanii* Cham.), Shirakannba (*Betula platyphylla*), Udaikannba (*Betula maximowicziana*), and Yaegawakannba (Koonoore, *Betula davurica* Pall.) belong to Betulaceae *Betula*. It is known that 35 species are belonged to *Betula*, and they are widely distributed from the temperate zone to the subarctic zone of the northern hemisphere.

Shirakannba (*Betula platyphylla*) is a deciduous high tree distributed in Hokkaido (the area above sea level 0 to 700 m) and the east area of Honshu from Gifu prefecture (the area above sea level 700 to 1,600 m). From Shirakannba, rhododendrin (it is sometimes referred to as betuloside), aceroside VII, aceroside VIII, acerogenin E, (−)-rhododendrol, 15-methoxy-17-O-methyl-7-oxoacerogenin E, and acerogenin K and the like are obtained.

Udaikannba (*Betula maximowicziana*), distributed in the central area of Hokkaido and Honshu, is also called as Makaba or Makannba. From endodermis of Udaikannba, acerogenin E, 16-hydroxy-17-O-methyl-acerogenin E and the like are obtained.

Dakekannba (*Betula ermanii* Cham.) is distributed in Hokkaido, from central to northern part of Honshu, and Shikoku island in Japan. Outside of Japan, it is distributed in Korea peninsula, the east north part of China, Nei Mongol, Sakhalin, Kurile island, Kamchatskaya. From the trunk endodermis of Dakekannba, acerogenin E ((3R)-3,5'-dihidoloxy-4'-methoxy-3',4"-oxo-1,7-diphenyl-1-heptenone) and the like are obtained. Yaegawakannba (Koonoore, *Betula davurica* Pall.) is distributed in Hokkaido and Honshu in Japan, and Korea, China, Ussriisk, Amurskaya and the like outside of Japan. From the endodermis of Yaegawakannba, acerogenin E, 17-O-methyl-7-oxoacerogenin E, 15-methoxy-17-O-methyl-7-oxoacerogenin E and the like are obtained.

Hannoki (*Alnus japonica* Steud.) belongs to Betulaceae *Betula*, and distributed in all over Japan. From fruits of Hannoki, acerogenin L or the like are obtained. From *Boswellia ovalifoliolata* distributed in all over India, acerogenin C (3α-hydroxyous-12-ene) or the like are obtained.

The present invention is also the pharmaceutical preparation for preventing and/or treating bone disease comprising the diarylheptanoid compounds shown in the above formula (I) and derivatives thereof, as the active ingredient. Here, the term "derivative" includes the diarylheptanoid compound, its half-mer, the glycosides thereof, the physiologically acceptable salts thereof, and the hydrates thereof. The pharmaceutical composition for preventing and/or treating bone disease also has increasing activity of the alveolar bones.

Furthermore, the present invention is the pharmaceutical preparation for preventing and/or treating bone disease comprising the diarylheptanoid compounds shown in the above formula (IV) and derivatives thereof, as the active ingredient. Here, the term "derivative" has the same meaning as mentioned above. The pharmaceutical preparation for preventing and/or treating bone disease also has increasing activity of the alveolar bones.

Here, the amounts contained in the pharmaceutical composition for preventing and/or treating bone disease is preferably from 0.1 to 100 mg per dose, more preferably from 0.1 to 50 mg per dose, specifically preferable from 0.3 to 10 mg per dose.

The pharmaceutical preparation for preventing and/or treating bone disease has preferably a dosage form for oral administration, and it is preferably selected from the group consisting of tablets, powders, capsules, granules, pills, troches, liquids, and spherically-formed gels impregnated the liquid agent.

As the bone diseases to which the pharmaceutical preparation having such dosage form of the present invention is effective, there are mentioned these caused by the endogenous bone disease, the exogenous bone disease, or malnutrition. To the endogenous bone disease, the preparation of the present invention can be preferably used for the disease, when it is caused by the weakened osseous tissue attributed in the bone disease selected from the group consisting of pre-osteoporosis, osteoporosis, hypercalcemia, hyper PTH syndrome, Paget disease, arthritis, rheumatoid arthritis, bone metastasis of breast cancer, osteomalacemia, malignant neoplasm, and malnutrition. Also, to the exogenous disease, the preparation of the present invention is preferably used for the disease, when it is caused from traumatic fracture, fatigue fracture, and so forth. The preparation is preferably also used for decreased alveolar bone.

Particularly, since the present preparation promotes the bone formation by promoting the osteoblast differentiation, it has highly effective to prevent to appear such diseases or relieve their symptoms.

The present invention is also the functional food comprising at least one selected from the group consisting of the above-mentioned compounds, the glycosides thereof, the physiologically acceptable salts thereof, and the hydrates thereof. The functional food of the present invention may comprise any extracts obtained from the above-mentioned plants such as Megusurinoki and so forth. Here, the physiologically acceptable salts thereof, and the hydrates thereof are the same as those described above.

The functional food of the present invention is also preferably used to adjunct to prevention and/or treatment of the bone disease. Wherein, the amounts of one selected from the group consisting of the compounds, physiologically acceptable salt thereof and the hydrate thereof is preferably 0.1 to 5 mg per 100 g of the functional food, more preferably 0.1 to 3 mg per 100 g. The functional food of the present invention includes them in the content ranged from 0.3 to 1 mg has the highest effect to adjunct to prevention of the bone disease and/or treatment.

Furthermore, the present invention is a health food containing at least one selected from the group consisting of the above-mentioned compounds, the physiologically acceptable salt thereof, and the hydrate thereof. The health food of the present invention may comprise any extracts obtained from the above-mentioned plants such as Megusurinoki and so forth. Wherein, the physiologically acceptable salts thereof, and the hydrates thereof are the same as those described above.

The health food of the present invention is also preferably used to adjunct, to prevention of the bone disease and/or treatment. Wherein, the content amount of one selected from the group consisting of the compounds, physiologically acceptable salt thereof and hydrate thereof is preferably 0.1 to 5 mg per 100 g, more preferably 0.1 to 3 mg per 100 g. The functional food of the present invention includes them in the content ranged from 0.3 to 1 mg has the highest effect to adjunct to prevention of the bone disease and/or treatment.

When the above-mentioned compounds, physiologically acceptable salt thereof, the hydrate thereof, the extract from the plants such as Megusurinoki and so forth is used to produce the functional food or health food, they enables easily to intake the ingredients having both effect to promote the osteoblast differentiation and bone formation in daily life.

According to the present invention, the functional food, the health food, the pharmaceutical composition for preventing and/or treating bone disease, and the pharmaceutical preparation for preventing and/or treating bone disease are provided.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
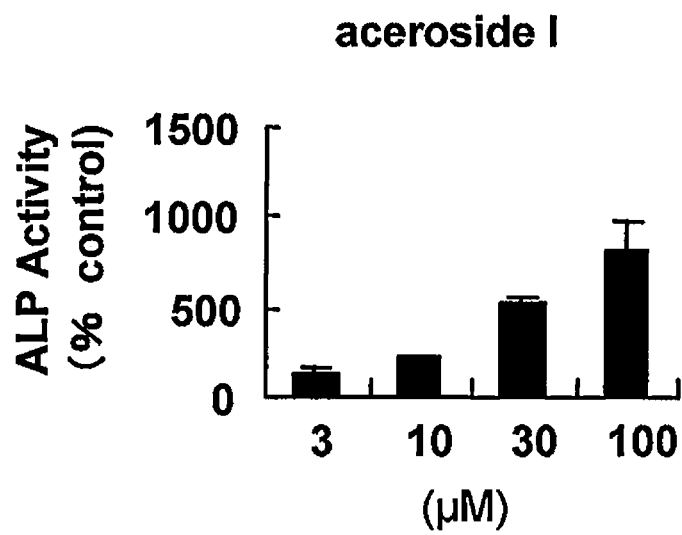
FIG. 1A shows the differentiation effect of aceroside I to osteoblast, MC3T3-E1 cells (changes of ALP activities)
Figure 1B:
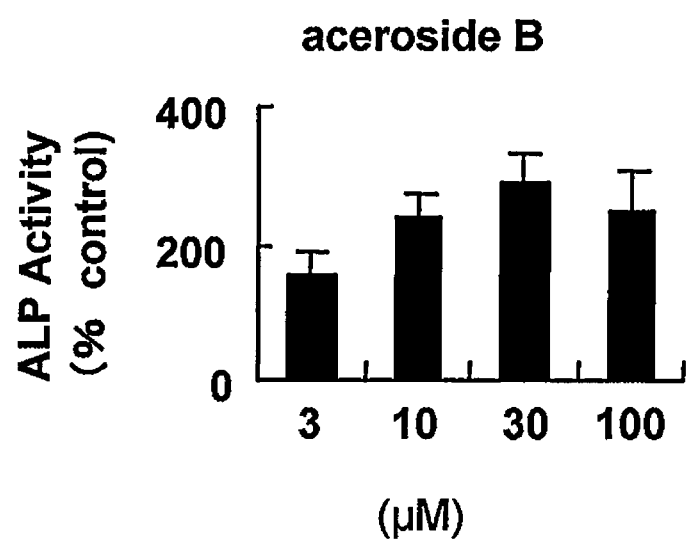
FIG. 1B shows the differentiation effect of aceroside $B_1$ to the same cells as those used in FIG. 1A (changes of ALP activities)
Figure 1C:
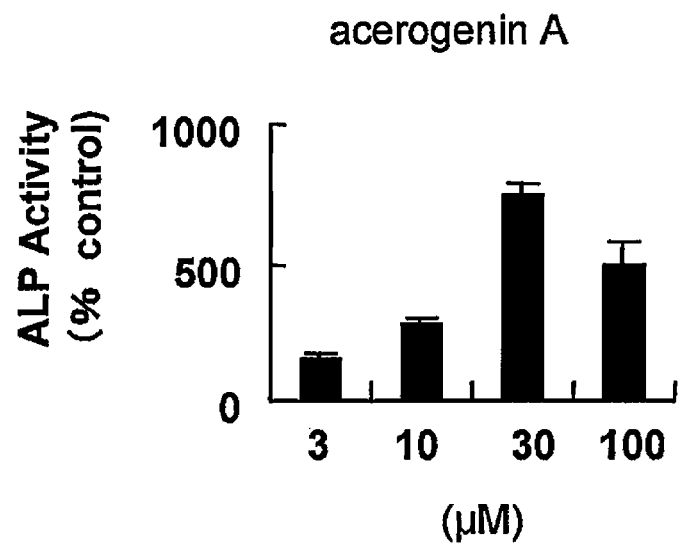
FIG. 1C shows the differentiation effect of acerogenin A to the same cells as those used in FIG. 1A (changes of ALP activities)
Figure 1D:
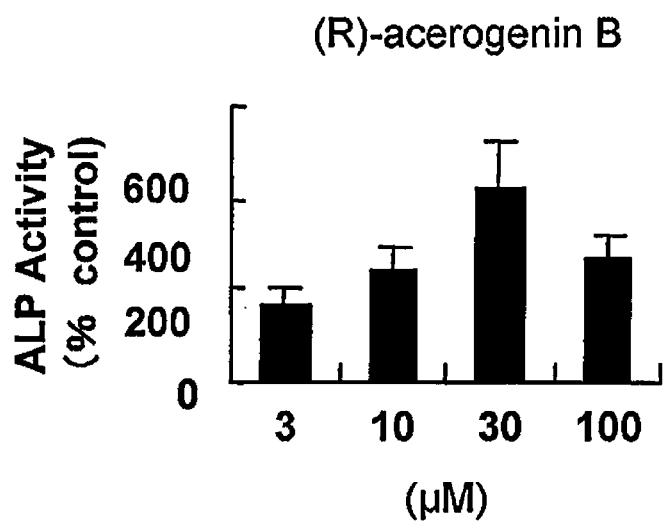
FIG. 1D shows the differentiation effect of (R)-acerogenin B to the same cells as those used in FIG. 1A (changes of ALP activities)

The present invention is explained in detail hereinafter.

The first aspect of the present invention is the pharmaceutical composition for preventing and/or treating bone disease comprising at least one selected from the group consisting of the diarylheptanoid compound shown in the following formula (I) and the derivatives thereof.

[Chemical formula 17]

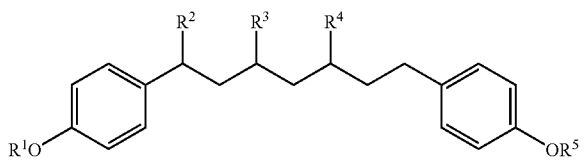

(I)

In the formula (I), $R^1$ is the functional group selected from the group consisting of a hydrogen atom, an alkyl group having the carbon number 1 to 3, the monosaccharide and disaccharide; $R^2$, $R^3$, $R^4$ are independently one selected from the group consisting of a hydrogen atom, an oxygen atom, hydroxyl group, the monosaccharide and the disaccharide; $R^5$ is the functional group selected from the group consisting of a hydrogen atom, alkyl group having 1 to 3 carbon atoms, the monosaccharide and the disaccharide, or is may be bound on meta-position against heptylene group bound on another aryl group to form a ring. Each aryl group may be respectively bound between carbons located in meta-position against the heptylene group to form a ring.

When $R^5$ is not bound to another aryl group to form the ring, $R^3$ is the hydroxyl group, and all of $R^1$, $R^2$, $R^4$ and $R^5$ are hydrogen atoms.

When, $R^5$ in the formula (I) is bound to the heptylene group on another aryl group at meta position to form the ring, it is the compound shown in the following formula (II). When two aryl group shown in the formula (I) are respectively bound to the heptylene group on another aryl group at meta position to form the ring, it is the compound shown in the following formula (III).

[Chemical formula 18]

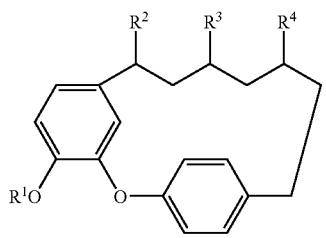

(II)

In the formula (II), $R^1$ is preferably a hydrogen atom or glycosyl group; $R^2$, $R^3$, and $R^4$ are preferably the functional group selected from the group consisting of a hydrogen atom, an oxygen atom, the monosaccharide and the disaccharide independently.

[Chemical formula 19]

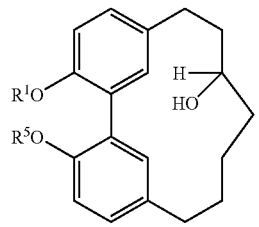

(III)

In the formula (III), $R^1$ and $R^5$ are preferably a hydrogen atom or methyl group independently.

As these compounds, physiologically acceptable salts thereof, hydrates thereof, and glycosides thereof may be used depending on the needs; in particular, when the highly water-soluble salts thereof such as hydrochloride and the like are formed, by using such salts, they show higher osteoblast differentiation and osteogenesis promotion effects.

The present invention is also a pharmaceutical composition for preventing and/or treating bone disease comprising at least one selected from the group consisting of the half-mer compound shown in the following formula (IV), the physiologically acceptable salt thereof, and the hydrate thereof as the active ingredient.

[Chemical formula 20]

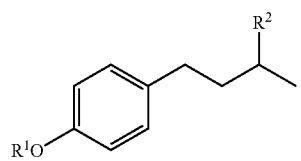

(IV)

In the formula (IV), $R^1$ is preferably a hydrogen atom, and $R^2$ is preferably hydroxyl group or methyl group.

As the compound shown in the formula (I), it is preferably the compound shown in the following formula (Ia).

[Chemical formula 21]

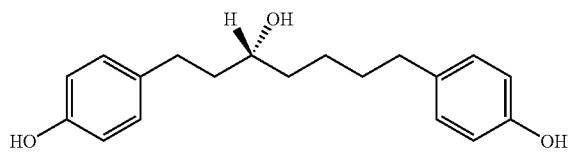

(Ia)

As the compound shown in the formula (II) and the derivatives thereof, there are mentioned such as acerogenin A shown in the following formula (IIa), (R)-acerogenin B shown in the formula (IIb), aceroside I shown in the formula (IIc), aceroside $B_1$ shown in the formula (IId), aceroside III shown in the formula (IIe), aceroside D shown in the formula (IIf), aceroside IV shown in the formula (IIg), and aceroside M shown in the formula (IIh); they are preferably used because they have high activities to promote the osteoblast differentiation to promote bone formation.

[Chemical formula 22]

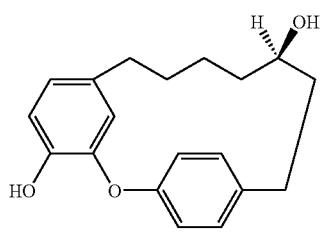

(IIa)

[Chemical formula 23]

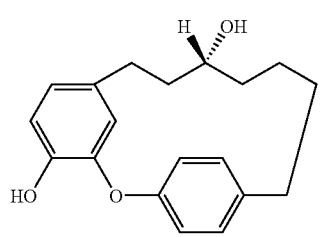

(IIb)

[Chemical formula 24]

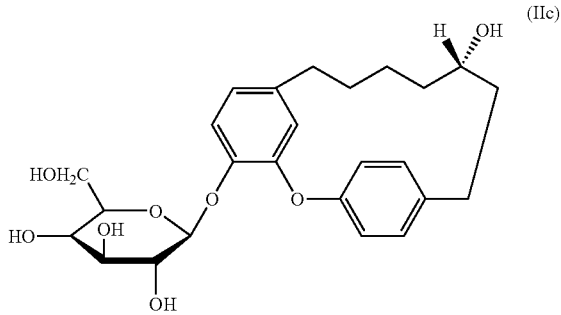

(IIc)

-continued

[Chemical formula 25]

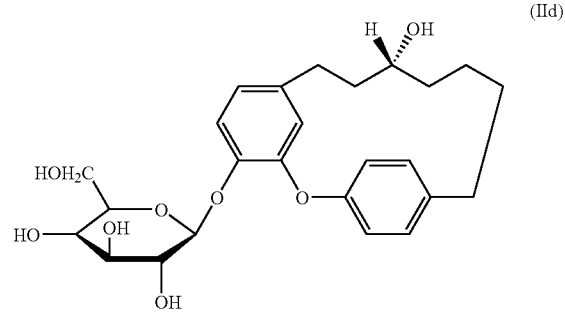
(IId)

[Chemical formula 26]

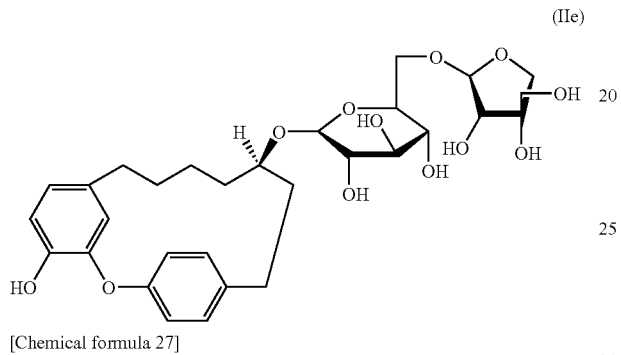
(IIe)

[Chemical formula 27]

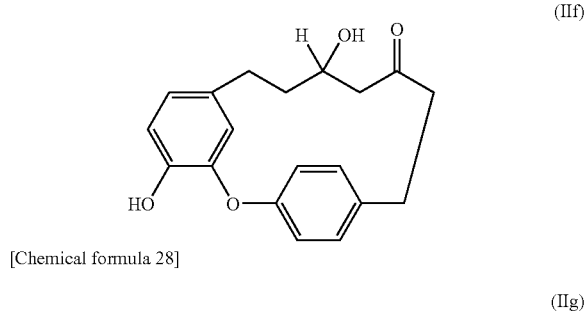
(IIf)

[Chemical formula 28]

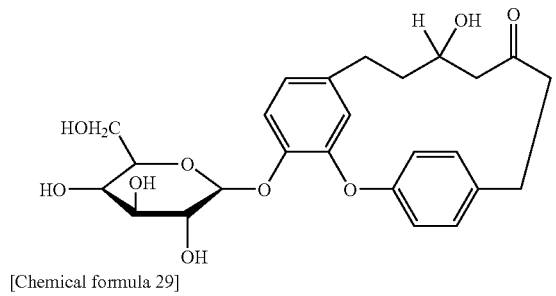
(IIg)

[Chemical formula 29]

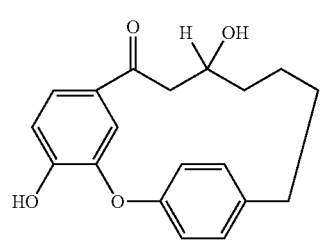
(IIh)

AS the compound shown in the formula (III) and the derivatives thereof, acerogenin K shown in the following formula (IIIa) and (+)-Rhododendrol shown in the following formula (IVa) are preferable used.

[Chemical formula 30]

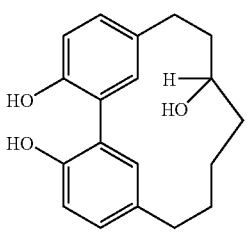
(IIIa)

[Chemical formula 31]

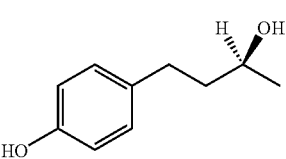
(IVa)

Note that the physiologically acceptable salt thereof, hydrate thereof, and glycoside thereof are also as mentioned above.

A variety of diarylheptanoid compounds, half-mer thereof, and the derivative thereof (compound and the like) as mentioned above may be used optionally for producing the pharmaceutical preparation solely or in combination of two or more, as needed.

The compounds shown in the above-mentioned formulae (I) to (IVa) and derivatives thereof may be obtained through the known method or pursuant to it. These may be purchased from the commercially available ones to be used. The diarylheptanoid compounds as mentioned above, the half-mer thereof, physiologically acceptable salts thereof, hydrates thereof, and the glycosides thereof may be obtained from the plant sources described above by extraction and isolation. For example, afford an instance of the isolation of aceroside I, aceroside III, aceroside $B_1$ and the like from Megusurinoki is explained.

The bark of Megusurinoki is collected to dry. After drying, it is crashed and the lipophilic components are extracted by using highly hydrophobic solvents such as n-hexane, and the like. Then, residue of the extracted is extracted by the solvent such as methanol, preferably at room temperature. The extracts are partitioned between water and an organic solvent, for example, ethyl acetate, to obtain aqua phase and organic phase.

The organic phase is subjected to a column chromatography by using silica gel, and then eluted by using n-hexane-ethyl acetate and ethyl acetate-methanol as eluents, increasing polarity of the eluent sequentially to fractionate. From one fraction among these obtained here (for example, Fraction 9), the glycosides shown in the above-mentioned formulae (IIc) to (IIe) and (IIg) may be obtained by using the following procedure. From different fraction from that used to obtain the glycoside (for example Fraction 7), the compounds shown in the above-mentioned formulae (Ia), (IIa), (IIb), (IIIa) and (IVa) may be obtained by using the following procedure.

In order to obtain the glycoside, the fraction (Fraction 9) is further subjected to the column chromatography using silica gel and ethyl acetate-methanol as the eluent. A part of the obtained fractions (for example, Fraction 9-2) is subjected to the column chromatography using octadecyl silica gel (ODS). Subsequently, they are further subjected to ODS column chromatography-high performance liquid chromatography (HPLC) (developing solvent acetonitrile:water=3:7, flow rate 3.0 mL/min. By this separation, the compound such as shown in the formulae (IIc) to (IIe) and (IIg) may be obtained.

Another fraction (Fraction 7) is again subjected to the silica gel column chromatography to fractionate. A part of the obtained fractions (for example, Fraction 7-1 and 7-2) are subjected to HPLC (ODS silica gel column is used) by using methanol-water as the eluent. Then, the compound such as shown in the formulae (Ia), (IIa), (IIIa) and (IVa) may be isolated in preparative.

As described above, from the extracts from Megusurinoki, the compounds shown in the formulae and the derivatives thereof may be obtained. Even use other plants as the source except those described above, the compounds such as shown in the formulae and the derivatives thereof may be obtained by using the similar method.

Obtained components are subjected to a mass spectrometry (MS), nucleic magnetic resonance (NMR), and the like to have spectrum data from them. Comparing them to literature data, they may be identified what structure they have.

The compounds shown in the formulae (I) to (IVa), the physiologically acceptable salt thereof, the hydrate thereof, and mixture thereof as described above may be used to produce the pharmaceutical preparation describe in below.

When aceroside I is solely used to prepare the pharmaceutical preparation, the physiologically acceptable salt thereof, the hydrate thereof, and mixture thereof obtained as described above are treated by using the conventional method, and then mixed with excipients and so forth described later.

When combinations of aceroside I and other diarylheptanoid, particularly, a variety of acerogenin, are used, the ratio of aceroside I is 1, and the ratios of others are desirably from 0.1 to 10, and then mixed. Then, the mixture is used to prepare the pharmaceutical preparation similar way to use aceroside I solely.

The second aspect of the present invention is a pharmaceutical preparation comprising the pharmaceutical composition as the active ingredient. As these pharmaceutical preparations, there are mentioned such as parenteral preparations such as injectables, suppositories, aerosols, percutaneous and so forth, tablets, powders, capsules, pills, trochiscus, solutions and other dosage forms. Wherein, the above-mentioned tablet includes sugar coated tablets, coated tablets, and buccal tablets; the capsule includes both of hard and soft capsules. The granules contain coated granules. The above-mentioned solution contains suspensions, emulsions, syrups, elixirs, and so forth, and the syrup includes also dry syrups.

As other dosage forms, there are mentioned such as solutions of the pharmaceutical compositions, gel preparations wherein the agarose beads are impregnated in the solutions, and the like.

Note that each preparation includes not only non-sustained preparation, but also sustained preparations.

These preparations may be formulated according to the known procedure by using pharmacologically acceptable carrier, excipient, disintegrator, lubricant, colorant, and so forth, for formulating the preparation, described on Japanese Pharmacopoeia.

As these carriers or excipients, for example, there are mentioned such as lactose, glucose, sucrose, mannitol, potato starch, corn starch, calcium carbonate, calcium phosphate, calcium sulfate, crystalline cellulose, powdered glycyrrhiza extract, powdered gentian, and so forth.

As a binder, for example, there are mentioned such as the starch, tragacanth gum, gelatin, syrup, polyvinyl alcohol, polyvinylether, polyvinylpyrrolidone, hydroxypropylcellulose, methylcellulose, ethylcellulose, carboxymethylcellulose, and so forth.

As the disintegrator, for example, there are mentioned such as starch, agar, powdered gelatin, sodium carboxymethylcellulose, calcium carboxymethylcellulose, crystalline cellulose, calcium carbonate, sodium bicarbonate, sodium alginate and so forth; as the lubricant, for example, there are mentioned such as magnesium stearate, talc, hydrogenated vegetable oil, macrogol and so forth.

The colorant, which is acceptable to be added to the pharmaceutical preparation, can be used with no limitation. Except these additives, a corrigent and so forth can be used depending on the necessity.

When formulating the tablet or the granule, if necessary, they may be coated by using sucrose, gelatin, hydroxypropylcellulose, purified shellac, gelatin, glycerin, sorbitol, ethylcellulose, hydroxy-propylcellulose, hydroxypropylmethylcellulose, polyvinylpyrrolidone, acetate cellulose phthalate, hydroxypropylmethylcellulose phthalate, methylmethacrylate, methacrylate polymer, and so forth to have single coating or plural coatings.

Furthermore, the capsule can be prepared by encapsulating the granule or powdered preparation into the capsule made of ethylcellulose, gelatin, and so forth.

When the injectable is prepared by using the above-mentioned compound, the physiologically acceptable salt thereof, or the hydrate thereof, a PH regulator, a buffering agent, a stabilizer, a solubilizing agent, and so forth may be added as needed.

When the preparation for preventing and/or treating bone disease as mentioned above is administrated to a patient, the dosage is depending on conditions such as thickness of the symptom, age, weight, and health status and so forth. In general, the preparation is administrated for an adult in the parenteral or non-parenteral route, at the dosage of 1 mg/kg to 2,000 mg/kg, preferably 1 mg/kg to 1,000 mg/kg once a day or more. Number of administration and amounts a day can be adjusted depending on the conditions described above optionally.

When the preparation is administrated to the patient to form the alveolar bone, for example, solutions of the purified or crude extracts, or the liquid containing them may be prepared for impregnation of the agarose beads in them, and then the impregnated agarose beads may be surgically embedded to the affected area.

When the pharmaceutical preparation comprises aceroside I only, or aceroside I and other diarylheptanoids, for example, rhododendrol, as the active ingredient, the amounts of aceroside I contained in the composition is preferably 0.1 to 100 mg, more preferably 0.1 to 50 mg, and further more preferably 0.3 to 10 mg.

If the amount of aceroside I or other diarylheptanoid compounds is less than the lower limit, the osteogenesis accelerating effect is poorly shown, and it is added at the amount more than the upper limit, the effect worth the added amount is not shown. Alternatively, when the amount excesses the upper limit, it may cause potential undesirable side effect to a living body being administrated it.

The functional food having the effects preventing and/or treating bone disease as mentioned above, the third aspect of the present invention, or the health food, the fourth aspect of the present invention, is provided by adding the composition of the present invention desirably.

In the specification, the term "functional food" is defined as the food which comprises components enabling to provide benefits more than that from the food itself essentially contains nutrients, when a person takes the food.

In this specification, the term "health food" is defined as a generic term for foods used to contribute for the preservation and improvement of health in general, and includes supplement that assist to intake nutrient components short in daily.

The composition described above is added to, for example, breads, cookies and biscuits, wheat and miscellaneous cereals for being supplemented to rice, noodles such as Japanese wheat noodle, soba noodle, and pasta, dairy product such as cheese, yogurt, jam, mayonnaise, processed soy product such as soybean paste, soy source, tea, coffee and cocoa, nonalcoholic beverage such as soft drinks and fruits juice, alcoholic beverage such as medicated liquor, snacks such as candy, and chocolate, chewing gum, Japanese cracker, sweets made from azuki-bean such as azuki-bean jelly, to produce the functional food.

When the composition is added to the yogurt, soy source, beverages and so forth, an auxiliary agent for solubilizing or the stabilizer may be added optionally to avoid the precipitation of crystalline of the present composition in them.

Also, the composition of the present invention may be used solely or in combination of two or more, and to formulate the powdered agent, the granule, the tablet or the capsule, to prepare the health food.

Here, in order to form the powdered composition of the present invention, the extract obtained in the production process may be condensed, and dried by using the method such as lyophilization, spray-drying, vacuum-drying and so forth; and then dried extract is pulverized into fine powder by using a sample mill, blender, mixer or the like. Corn starch, dextrin, cyclodextrin, oystershell powder may be added to the powder as needed.

Alternatively, the binder is optionally added to the powder obtained as described above and compressed to formulate the tablet. After formulation of the tablet, it may be coated by using the coating agent such as sucrose, gelatin and so forth to formulate the sugar-coated tablet, or coated by other coating agent to formulate enteric coated tablet.

Furthermore, the powder obtained as describe above may be granulated by using the conventional method to formulate the granule. The powder or granule as mentioned above is encapsulated into capsules in a proper amount to formulate the capsule.

EXAMPLE

The present invention is explained in detail by using examples below, however, the present invention is not limited to them.

Example 1

Purification and Isolation of Diarylheptanoid

Aceroside I, aceroside $B_1$ acerogenin A and (R)-acerogenin B were purified as follows.

(1-1) Preparation of Extracts for a Column Chromatography

Dried bark of Megusurinoki (450 g) were extracted 3 times by using 2.5 L of n-hexane, and filtrated to remove residue. Then, the filtrates were evaporated under reduced pressure to remove solvent in the filtrate, and n-hexane extracts (3.4 g) were obtained. The residue which was extracted by n-hexane and filtrated were extracted another 3 times by using 2.5 L of methanol, and filtrated to remove the residue. Then, the filtrate was evaporated under reduced pressure to remove the solvent in the filtrates, and methanol extracts (63.6 g) were obtained.

The methanol extracts were extracted by using mixed solvent in which the ratio of ethyl acetate:water=1:1, and organic phase (ethyl acetate phase, 26.2 g) and aqueous phase were obtained. The aqueous phase was further extracted by using n-butanol, and the organic phase (n-butanol phase, 26.6 g) and the aqueous phase (4.5 g) were obtained.

(1-2) Purification of Aceroside I, Aceroside III, and Aceroside $B_1$

Ethyl acetate phase (25 g) was subjected to a silica gel column chromatography, and eluted by using elution buffers for gradient elution. As the elution buffers, n-hexane:ethyl acetate and ethyl acetate:methanol were used. Firstly, the elution was performed by using n-hexane:ethyl acetate, sequentially increasing the polarity of the elution buffer between the range of n-hexane:ethyl acetate=1:0 and 0:1. Next, the elution was performed by using ethyl acetate:methanol instead of n-hexane:ethyl acetate, sequentially increasing the polarity of the elution buffer between the range of ethyl acetate:methanol=1:0 and 0:1.

By fractionation, Fr. 1 to Fr. 9 were obtained, and then, Fr. 9 was again subjected to the silica gel column chromatography. As the elution buffer, ethyl acetate:methanol was used, and the elution was performed, sequentially increasing the polarity of the elution buffer between the range of ethyl acetate:methanol=4:1 and 0:1. Fr. 9-1 to 9-5 were obtained.

Fr. 9-2 was subjected to ODS column chromatography and the eluate was fractionated Fr. 9-2-1 and 9-2-2. Fr. 9-2-2 was again subjected to the ODS column chromatography and the eluate was fractionated into Fr. 9-2-2-1 to 9-2-2-5. Among them, Fr. 9-2-2-4 and 9-2-2-5 were subjected to HPLC, and eluted under the following elution condition 1 to obtain aceroside I, aceroside III, and aceroside $B_1$.

<Elution Condition 1>
Column: Pegasil ODS-II 10φ×250 mm
Elution buffer: MeCN: $H_2O$=3:7
Flow rate: 3.0 mL/min Fr. 7, the ethyl acetate phase, was subjected to the silica gel column chromatography, and eluate was fractionated from Fr. 7-1 to 7-11. Among them, Fr. 7-1 and 7-2 were subjected to HPLC, and eluted under the following elution condition 2 to isolate and obtain acerogenin A, (R)-acerogenin B, acerogenin K, (−)-centrolobol, and (+)-rhododendrol.

<Elution Condition 2>
Column: Pegasil ODS-II 10φ×250 mm
Elution buffer: MeOH: $H_2O$=65:35 (AcOH 0.1%)
Flow rate: 3.0 mL/min (1-3) Identification of Obtained Compounds and Glycosides Each compounds and glycosides obtained as described above were identified by comparing spectrum data to the literature data.

(1-3-1) Spectrum Data of Aceroside I

Spectrum data obtained by analysis of HR-FAB-MS and $^1$H-NMR (400 MHz, $C_5D_5N$) was compared to those described in the reference (1), and identified.

HR-FAB-MS: $C_{25}H_{32}O_8Na$ [M+Na]$^+$ 483.19950, m/z 297 [M-$C_6H_{11}O_5$]$^-$, $^1$H-NMR (400 MHz, $C_5D_5N$) δ: 1.00 (1H, m, 9-H), 1.12 (1H, m, 10-H), 1.26 (2H, m, 8,9-H), 1.39 (1H, m, 10-H), 1.50 (1H, m, 8-H), 1.71 (1H, m, 12-H), 2.13 (1H, m, 12-H), 2.42 (2H, m, 7-$H_2$), 2.75 (1H, m, 13-H), 2.94 (1H, m, 13-H), 3.53 (1H, m, 11-H), 4.18 (1H, m, 5'-H), 4.43 (4H, m, 2', 3', 4',6'-H), 4.59 (1H, dd, J=11.8, 1.7 Hz, 6'-H), 5.85 (1H, d, J=6.6 Hz, 1'-H), 5.94 (1H, d, J=1.0 Hz, 6-H), 6.69 (1H, dd, J=8.0, 1.0 Hz, 4-H), 6.97 (1H, dd, J=8.1, 2.2 Hz, 16-H or 18-H), 7.21

(1H, d, J=3.7 Hz, 15-H or 19-H), 7.24 (1H, d, J=2.2 Hz, 16-H or 18-H), 7.29 (1H, dd, J=8.3, 1.7 Hz, 15-H or 19-H), 7.55 (1H, d, J=8.3 Hz, 3-H).

(1-3-2) Spectrum Data of Aceroside III

Spectrum data obtained by analysis of ESI-MS and $^1$H-NMR (400 MHz, $C_5D_5N$) was compared to those described in the reference (2), and identified.

ESI-MS: m/z 615 [M+Na]$^+$, 591 [M-H]$^-$, $^1$H-NMR (400 MHz, $C_5D_5N$) δ: 0.86 (1H, m, 9-H), 1.08 (2H, m, 9,12-H), 1.22 (1H, m, 8-H), 1.43 (1H, m, 8-H), 1.54 (2H, m, 10,12-H), 2.36 (2H, m, 7,10-H), 2.50 (1H, m, 7-H), 2.87 (1H, m, 13-H), 3.14 (1H, m, 13-H), 3.57 (1H, m, 11-H), 4.02 (1H, m, 2'-H), 4.11 (2H, m, 4',5'-H), 4.14 (2H, s, 5"-H), 4.23 (2H, m, 3',6'-H), 4.35 (1H, d, J=9.3 Hz, 4"-H), 4.60 (1H, d, J=9.3 Hz, 4"-H), 4.77 (1H, d, J=2.1 Hz, 2"-H), 4.80 (2H, m, 1',6'-H), 5.75 (1H, d, J=2.4 Hz, 1"-H), 5.99 (1H, d, J=2.1 Hz, 6-H), 6.72 (1H, dd, J=7.9, 2.1 Hz, 4-H), 7.22 (3,16,18-H), 7.27 (1H, d, J=7.9 Hz, 15-H or 19-H), 7.75 (1H, d, J=8.2 Hz, 15-H or 19-H).

(1-3-3) Spectrum Data of Aceroside $B_1$

Spectrum data obtained by analysis of ESI-MS and $^1$H-NMR (400 MHz, $C_5D_5N$) was compared to those described in the reference (3), and identified.

ESI-MS: m/z 483 [M+Na]$^+$, 495 [M+Cl]$^-$, $^1$H-NMR (400 MHz, $C_5D_5N$) δ: 0.96 (1H, m, H-10), 1.18 (1H, m, H-11), 1.48 (3H, m, H-10, 11 and 12), 1.66 (1H, m, H-8), 1.68 (1H, m, H-12), 1.73 (1H, m, H-8), 2.48 (1H, m, H-13), 2.64 (1H, m, H-13), 2.69 (1H, m, H-7), 2.99 (1H, m, H-7), 5.82 (1H, d, J=4.4 Hz, H-1'), 6.73 (1H, d, J=8.1 Hz, H-4), 6.91 (1H, d, J=8.3 Hz, H-16 or 18), 7.11 (1H, d, J=8.3 Hz, H-15 or 18), 7.54 (1H, d, J=8.3 Hz, H-3).

(1-3-4) Spectrum Data of Acerogenin A

Spectrum data obtained by analysis of ESI-MS and $^1$H-NMR (400 MHz, $C_5D_5N$) was compared to those described in the reference (1), and identified.

ESI-MS: m/z 321 [M+Na]$^+$, 297 [M-H]$^-$, $^1$H-NMR (400 MHz, $C_5D_5N$) δ: 1.01 (1H, m, H-9), 1.13 (1H, m, H-10), 1.28 (2H, m, H-8 and 9), 1.40 (1H, m, H-10), 1.53 (1H, m, H-8), 1.72 (1H, m, H-12), 2.14 (1H, m, H-12), 2.47 (2H, m, $H_2$-7), 2.76 (1H, m, H-13), 2.95 (1H, m, H-13), 3.54 (1H, m, H-11), 5.97 (1H, d, J=2.0 Hz, H-6), 6.75 (1H, dd, J=8.1, 2.0 Hz, H-4).

(1-3-5) Spectrum Data of (R)-Acerogenin B

Spectrum data obtained by analysis of ESI-MS and $^1$H-NMR (400 MHz, $C_5D_5N$) was compared to those described in the reference (3), and identified.

ESI-MS: m/z 321 [M+Na]$^+$, 297 [M-H]$^-$, $^1$H-NMR (400 MHz, $C_5D_5N$): 0.79 (1H, m, H-10), 1.00 (1H, m, H-11), 1.23 (1H, m, H-10), 1.30 (1H, m, H-11), 1.50 (2H, m, $H_2$-8), 1.53 (1H, m, H-12), 1.76 (1H, m, H-12), 2.57 (1H, m, H-7), 2.63 (2H, m, H-7 and 13), 2.80 (1H, m, H-13), 3.07 (1H, m, H-9), 5.57 (1H, d, J=1.8 Hz, H-6), 6.63 (1H, dd, J=8.2, 1.8 Hz, H-4), 6.84 (1H, d, J=8.2 Hz, H-3), 6.93 (1H, dd, J=2.5, 8.2 Hz, H-16 or 18), 7.13 (1H, dd, J=2.5, 8.2 Hz, H-18 or 16), 7.23 (1H, dd, J=2.1, 8.2 Hz, H-15 or 19), 7.30 (1H, dd, J=2.1, 8.2 Hz, H-19 or 15).

(1-3-6) Spectrum Data of Acerogenin K

Spectrum data obtained by analysis of ESI-MS and $^1$H-NMR (400 MHz, $C_5D_5N$) was compared to those described in the reference (4), and identified.

ESI-MS: m/z 297 [M-H]$^-$, $^1$H-NMR (400 MHz, $C_5D_5N$) δ: 1.45 (1H, m, 11-H), 1.74-1.83 (2H, m, 11, 12-H), 1.90 (1H, m, 10-H), 1.95-2.10 (3H, m, 8,10,12-H), 2.46 (1H, m, 8-H), 2.51 (1H, m, 13-H), 2.88 (1H, d, J=16.8 Hz, 13-H), 3.00 (1H, d, J=17.1 Hz), 3.34 (1H, m, 7-H), 4.49 (1H, t, J=9.5 Hz, 9-H), 7.13-7.22 (4H, m, 4,5,15,16-H), 7.48 (1H, br.s, 18-H), 7.6 (br.s, 19-H: overlapped with solvent signal).

(1-3-7) Spectrum Data of Centrolobol

Spectrum data obtained by analysis of ESI-MS and $^1$H-NMR (400 MHz, $C_5D_5N$) was compared to those described in the reference (5), and identified.

ESI-MS: m/z 323 [M+Na]$^+$, 299 [M-H]$^-$, $^1$H-NMR (600 MHz, $C_5D_5N$) δ: 1.58 (1H, m, 5-H), 1.68 (2H, m, 4 and 6-H), 1.72 (3H, m, 4, 5 and 6-H), 1.98 (2H, m, 2-$H_2$), 2.61 (2H, m, 7-$H_2$), 2.89 (1H, m, 1-H), 3.04 (1H, m, 1-H), 3.88 (1H, br.d, J=3.8 Hz, 3-H), 7.16 (2H, d, J=8.6 Hz, 3" and 5"-H), 7.18 (2H, d, J=8.6 Hz, 3' and 5'-H), 7.19 (2H, d, J=8.9 Hz, 2" and 3"-H), 7.29 (2H, d, J=8.2 Hz, 2' and 6'-H), $^{13}$C-NMR (150 MHz, $C_5D_5N$) δ 26.0 (5-C), 31.9 (1-C), 32.5 (6-C), 35.5 (7-C), 38.4 (4-C), 40.8 (2-C), 70.3 (3-C), 116.2 (3' and 5'-C or 3" and 5"-C), 116.3 (3" and 5"-C or 3' and 5'-C), 129.9 (2' and 6'-C or 2" and 6"-C), 130.3 (2" and 6"-C or 2' and 6'-C), 133.5 (1"-C), 133.8 (1'-C), 157.0 (4' and 4"-C).

(1-3-8) Spectrum Data of (+)-Rhododendrol

Spectrum data obtained by analysis of ESI-MS and $^1$H-NMR (400 MHz, $C_5D_5N$) was compared to those described in the reference (6), and identified.

REFERENCES (1) M. Nagai, M. Kubo, M. Fujita, T. Inoue and M. Matsuo, Studies on the Constituents of Aceraceae Plants. II. Structure of aceroside I, a Glucoside of a Novel Cyclic Diarylheptanoid from *Acer nikoense* Maxim., Chem. Pharm. Bull., 26, 2805-2810 (1978).

(2) M. Nagai, M. Kubo, K. Takahashi, M. Fujita, and T. Inoue, Studies on the Constituents of Aceraceae Plants. V. Two Diarylheptanoid Glycosides and an Arylbutanol Apiosylglucoside from *Acer nikoense*., Chem. Pharm. Bull., 31, 1923-1928 (1983).

(3) T. Morikawa, J. Tao, I. Toguchida, H. Matsuda and M. Yoshikawa, Structures of New Cyclic Diarylheptanoids and Inhibitors of Nitric Oxide Production from Japanese Folk Medicine *Acer nikoense*, J. Nat. Prod., 66, 86-91 (2003).

(4) S. Nagumo, S. Ishizawa, M. Nagai and T. Inoue, Studies on the Constituents of Aceraceae Plants. XIII. diarylheptanoids and Other Phenolics from *Acer nikoense*, Chem. Pharm. Bull., 45, 1086-1089 (1996).

(5) M. Nagai, N. Kenmochi, M. Fujita, N. Furukawa and T. Inoue, Studies on the Constituents of Aceraceae Plants. VI. Revised Stereochemistry of (−)-Centrolobol, and New Glycosides from *Acer nikoense*, Chem. Pharm. Bull., 34, 1056-1060 (1986).

(6) B. Das, P. S. Rao, K. V. N. S. Srinivas and J. S. Yadav, Stereospecific Synthesis and Absolute Configuration of (+)-Rhododendrol, Phytochemistry, 33, 1529-1530 (1993).

Example 1

Differentiation of Osteoblast Cell (1-1) Agents and so Forth

Aceroside I, aceroside B1, acerogenin A and (R)-acerogenin B purified and identified as mentioned above were used. MC3T3-E1 cells, mouse pre-osteoblast cell strain, was purchased from RIKEN Cell Bank. Ascorbic acid, β-glycerophosphoric acid, magnesium chloride were purchased from SIGMA-ALDRICH Corp. α-MEM was purchased from Invitrogen Corporation (Cat. No. 11900-024). The 96 well-microplate and 100 mm φ dish were purchased from Nunc Inc. (Cat. Nos. 161093 and 172958).

p-nitrophenylphosphate, naphtol AS-MX phosphate, Fast Blue BB salt and Alizarin Red S were purchased from SIGMA-ALDRICH Corp. Ascorbic acid, β-glycerophosphoric acid, methanol, tartaric acid, citric acid, sodium acetate, sodium hydroxide, formalin, and ethanol were purchased from Wako Pure Chemical Industries, Ltd. MTT (3-(4,5-Dimethyl-2-thizaolyl)-2,5-diphenyl-2H-tetrazolium Bromide) agent was purchased from Wako Pure Chemical Industries, Ltd. Cell Counting Kit-8 was purchased from Dojindo Laboratories.

(2) Osteoblast Differentiation

MC3T3-E1 cells, pre-osteoblast cells, were suspended in α-MEM and plated in each well of the 96 well-microplate with $4 \times 10^3$ cells/well. Then, they were pre-incubated for 2 days at 37° C., 5% $CO_2$ incubator. On day 3 from the beginning of the pre-incubation, culture medium in the wells were changed to α-MEM containing each concentration of test sample, 50 μg/mL of ascorbic acid and 10 mM β-glycerophosphoric acid, and then incubated for 7 to 21 days. In the incubation, the culture medium in the wells was exchanged in every 3 or 4 days.

After the incubation period, the cells were fixed by using methanol. After drying the dish, activity of alkaline phosphatase (ALP), a marker enzyme of early stage osteoblast differentiation, was measured, and subjected to ALP staining.

In the measurement of ALP activity, a buffer containing 6.7 mM p-nitrophenylphosphate as a substrate, supplemented 2 mM magnesium chloride and 100 mM tris-HCl, pH 8.5. 100 μL of the buffer was plated in each well, incubated in 30 minutes at 37° C. Then, 100 μl of 0.1 N sodium hydroxide was added to the wells to terminate the reaction. After that, the absorbance at 405 nm was measured by using the plate reader and the absorbance value was used as ALP activity.

In ALP staining, the buffer containing 0.1 mg/ml naphtol AS-MX phosphate, 0.6 mg/ml fast blue BB salt, supplemented 2 mM magnesium chloride and 10 mM tris-HCl pH 8.5 was used. 50 μL of the buffer was added to each well of the 96 well-microplate and incubated for 30 minutes to 1 hour to stain.

After incubation of the same condition as described above, cytotoxicity was measured by using the Cell counting kit-8 or MTT according to the conventional method.

Calcification of osteoblast cells were confirmed by Alizarin red S staining.

Effects of aceroside I, aceroside B1, acerogenin A, (R)-acerogenin B were shown in FIGS. 1A to 1D. It was demonstrated that these four compounds and glycoside thereof enhanced ALP activity, and accelerated the differentiation of osteoblast in early stage.

As shown in FIG. 1A, ALP activity was dose-dependently enhanced when aceroside I was added. When other 3 were added, ALP activity was dose-dependently enhanced by 30 μM, but decreased at 100 μM.

(3) Cytotoxicity

Cytotoxicity was measured by using Cell Counting kit-8 or MTT according to conventional method, after MC3T3-E1 was incubated in the same conditions as (2) described above. Results were shown in FIGS. 2A to D.

Figure 2A:
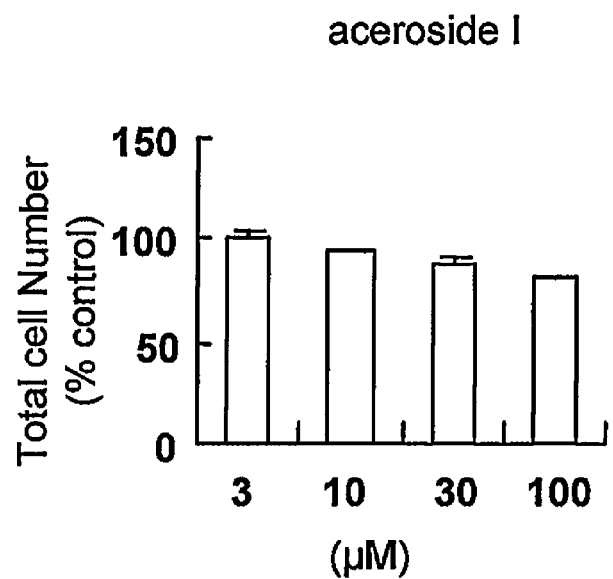
FIG. 2A shows the cytotoxicity of aceroside I to osteoblast differentiation by using the same cell used as FIG. 1A (changes of total cell numbers)

As shown in FIGS. 2A and C, cell numbers were not affected by addition of aceroside I or acerogenin A, but slightly decreased at high concentration. It was considered that the slight decrease was derived from the promotion of osteoblast differentiation, thereby growth of the cells was suppressed, and it is not caused by the cytotoxicity.

Figure 2B:
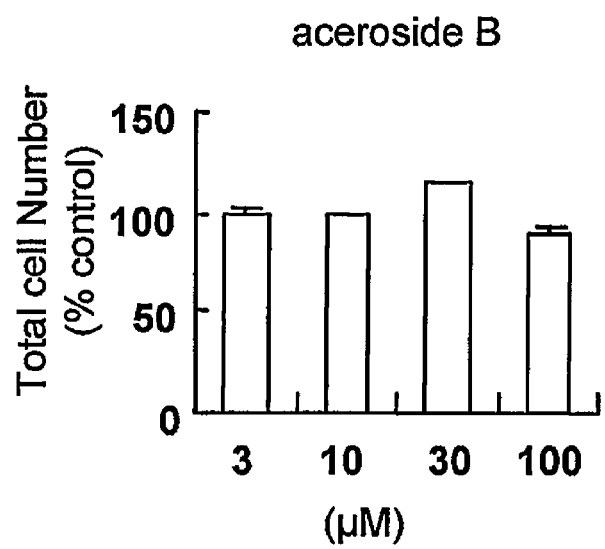
FIG. 2B shows the cytotoxicity of aceroside $B_1$ to the same cells as those used in FIG. 1A (changes of total cell numbers)
Figure 2C:
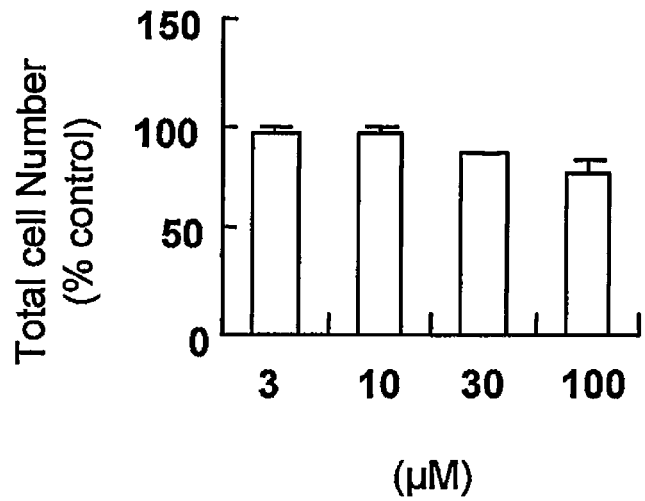
FIG. 2C shows the cytotoxicity of acerogenin A to the same cells as those used in FIG. 1A (changes of total cell numbers)
Figure 2D:
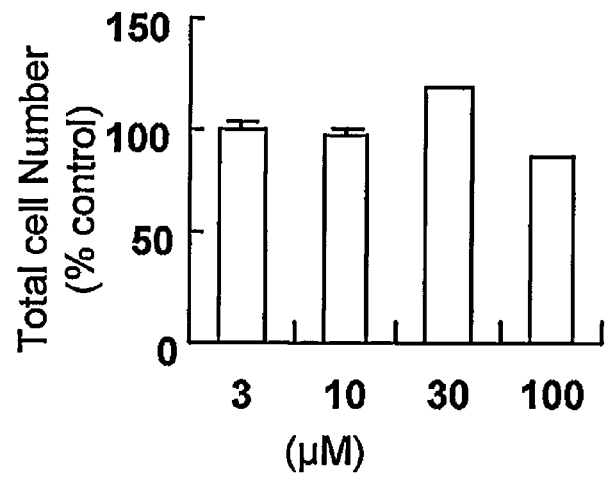
FIG. 2D shows the cytotoxicity of (R)-acerogenin B to the same cells as those used in FIG. 1A (changes of total cell numbers)
Figure 3:
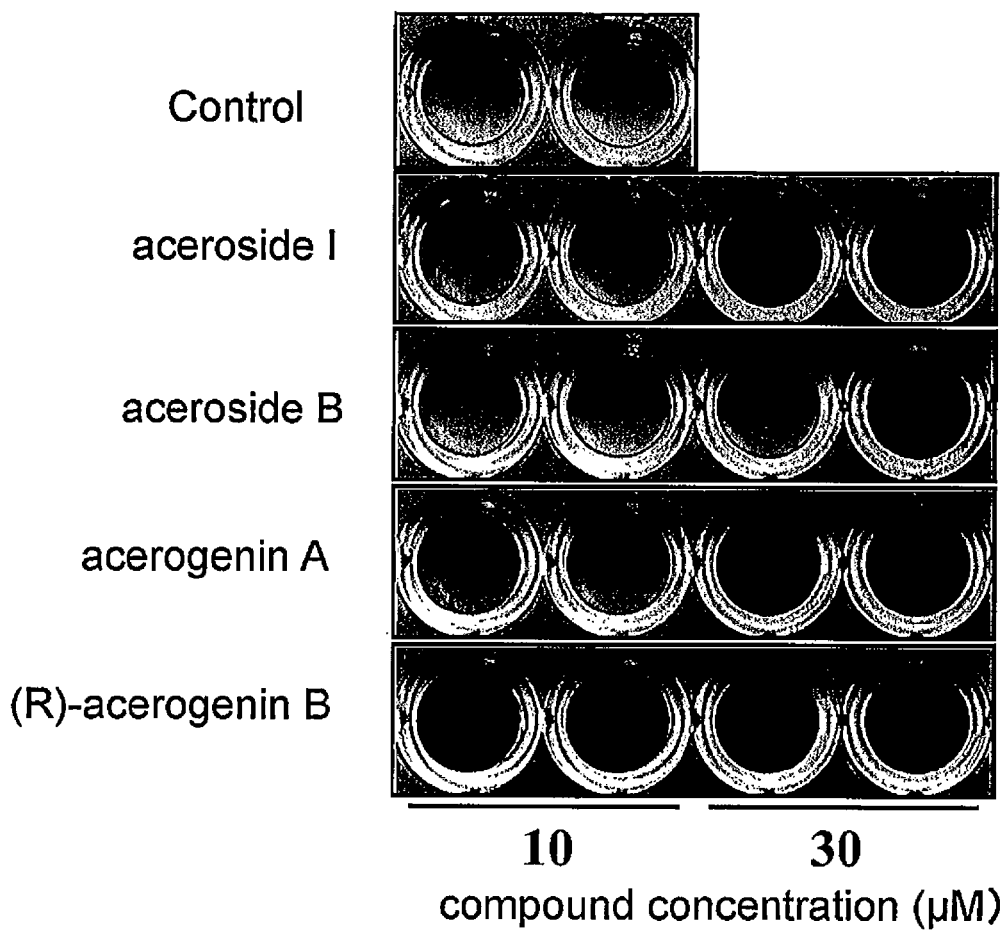
FIG. 3 shows the effect of calcification of calcium by aceroside I, aceroside $B_1$, acerogenin A and (R)-acerogenin B to the same cells as those used in FIG. 1A (changes of total cell numbers)

As shown in FIGS. 2B and D, when aceroside $B_1$ or (R)-acerogenin B was added, the cell number decreasing was not observed by 30 μM, and cell numbers were not affected by addition of them by 100 μM. Accordingly, the enhancement of ALP activities as mentioned above shows that these compounds selectively promoted osteoblast differentiation.

(4) Calcification of Calcium by Osteoblast

Effects of the above-mentioned four compounds and glycosides to the calcification of calcium by osteoblast were shown in FIG. 5. As shown in FIG. 5, control group was scarcely stained by Alizarin red S. On the other hand, treated group by the compounds or the glycosides were markedly stained. It showed that these promoted the osteoblast differentiation and also accelerated the calcification of calcium.

Alternatively, the calcification activity level of calcium by them was sequentially (R)-acerogenin B>aceroside I≡acerogenin A>aceroside $B_1$.

It was demonstrated that the calcification of calcium is disposed to be accelerated in dose-dependently, based on the thickness of the color after staining.

As stated above, it was considered that aceroside I, aceroside B1, acerogenin A and (R)-acerogenin promote the bone formation through the promotion of osteoblast differentiation. Accordingly, they are effective to prevent the generation of a variety of the bone osteopenia-like diseases, for example, osteoporosis, rheumatoid arthritis, periodontal diseases, Paget disease, bone metastasis of cancer, or the like. They have little side effects for treating these diseases so that they are expected to show excellent treatment effects.

Example 2

(1) Agents and so Forth

Dulbecco's physiological saline (hereinbelow, it is some times referred to as "D-PBS") were purchased from Dainippon Pharmaceutical Inc. Affi-Gel agarose beads (Affigel heparin Cat. No.: 15306173) were purchased from BioRad Laboratories.

Five days age of C57BL/6 mice were purchased from Sankyo Labo Service Corporation. As host mice, 10 to 15 weeks age of C57BL/6 mice (female) were purchased from Sankyo Labo Service Corporation, and used two per group. Since it is know that a kidney and an anterior chamber of eye hardly have immune response among organs in adult mice, it is not necessary to especially use nude mice in graft culture.

(2) Preparation of Agarose Beads Impregnated in Acerogenin A

Agarose beads impregnated in acerogenin A (hereinbelow, it is referred to as "acerogenin A-impregnated beads") were prepared as follows. acerogenin A was diluted to 100 μM (at final concentration) by using D-PBS. Affi-Gel agarose beads were washed by using PBS. Washed agarose beads were placed in the 1.5 mL Eppendorf tube with flat bottom and 100 μL of the acerogenin A solution was added into it. Then, the tube was incubated at room temperature for 45 minutes to impregnated acerogenin A into the agarose beads. Acerogenin-impregnated agarose beads obtained were used for embedding under dental pulp in below.

Alternatively, as negative control, agarose beads similarly to prepare the acerogenin A-impregnated beads but impregnated in D-PBS without acerogenin A (hereinbelow, it is referred to as "D-PBS-impregnated beads") were used.

(3) Embedding into Dental Pulp

Five days age of C45BL/6 mice, where their dental roots-periodontal tissue was just before formed, were anesthetized and sacrificed by decapitation. After excised lower jaw of them, the first molars in the lower jaw were excised with dental follicles. For the test group, three acerogenin A-impregnated agarose beads were embedded into the dental pulp of the excised teeth, the first molar in the lower jaw.

For the negative control group, three of the D-PBS-impregnated agarose beads prepared were embedded into another dental pulp of the excised teeth, the first molar in the lower jaw.

(4) Graft Culture

The excised teeth under which the acerogenin A-impregnated agarose beads were embedded and the teeth under which the D-PBS-impregnated agarose beads were embedded were respectively grafted under capsule of kidney of the host mice. The host mice were bred under the condition of 12 hours lighting, at room temperature, 25° C., free taking feed and water for 3 weeks.

After 3 weeks from grafting of the excised tooth, the host mice were sacrificed by dislocation of cervical vertebrae to excise the kidney to recover the cultured excised tooth (grafted tooth).

Dental roots-periodontal tissue formation (extension), periodontal ligament, and bone of the grafted tooth, which was recovered, were observed under a stereoscopic microscope, and then photographed by using CCD camera. Observed results of the graft tooth of each group after the graft culture were shown in FIG. 4.

Figure 4A:
FIG. 4A is a micrograph by using a stereoscopic microscope showing the status of removed tooth after transplantation in the negative control group (to which the agarose bead impregnated in Dulbecco's modified phosphate-buffered saline (hereinbelow, it is referred to as "D-PBS impregnated bead") is embedded)
Figure 4B:
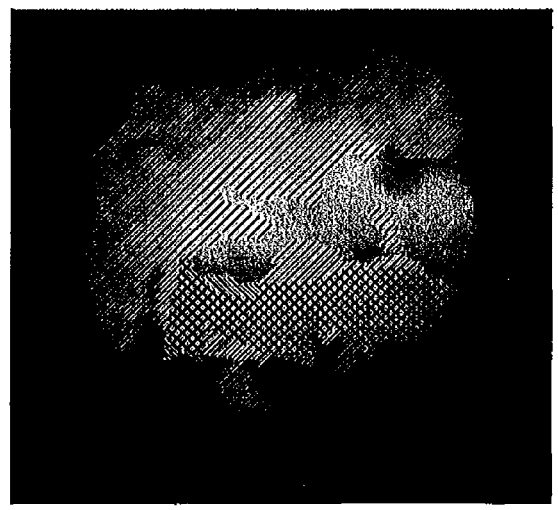
FIG. 4B is the micrograph by using the stereoscopic microscope showing the status of removed tooth after transplantation in the test group (to which the agarose bead impregnated in acerogenin A (hereinbelow, it is referred to as "acerogenin A impregnated bead") is embedded)).

As shown in FIG. 4, little extension of dental roots and bone formation were observed in the negative control group (see FIG. 4A, it was given the label, "PBS"). Formed alveolar bone was shown as hatching from upper right to lower left. In contrast, prominent extension of alveolar bone formation was observed in the test group (see FIG. 4B, it was given the label, "acerogenin A"), compared to the negative control group. Note that the part on to which reverse direction hatching was given shows the periodontal ligament area, and white part shows the teeth.

From these results, it was demonstrated that the pharmaceutical preparation comprising acerogenin A as the active ingredient had excellent promotion effect for alveolar bone formation (extension). Accordingly, it was demonstrated that the pharmaceutical preparation comprising acerogenin A as the active ingredient is very useful for promoting tissues around tooth such as the alveolar bone and the like so that it is higher effective for prevention and/or treatment of damages in these tissues.

Preparation Examples for Preventing and/or Treating the Bone Diseases

Next, preparation examples comprising the composition of the present invention, the present invention is not limited to them.

Preparation Example 1

| Components | Amounts used (g) |
| --- | --- |
| (R) - acerogenin B | 100 |
| Mannitol | 123 |
| Starch | 33 |
| Crospovidone | 12 |
| Microcrystalline cellulose | 30 |
| Magnesium stearate | 2 |

The components described above can be weighed respectively and homogeneously mixed, compressed, and then formulated as compression tablets of which weight is 300 mg.

Preparation Example 2

Hard Capsule

| Components | Amounts used (g) |
| --- | --- |
| Composition 1 | 40 |
| Lactose | 150 |
| Starch | 70 |
| Polyvinylpyrrolidone | 5 |
| Crystalline cellulose | 35 |

The components described above can be weighed respectively and homogeneously mixed, and formulated by being encapsulated into a hard capsule as the hard capsule preparation of which weight is 300 mg. Here, the composition 1 is a mixture of harmine and lactose at the ratio of 1:1. The composition used in the following preparation examples 3 to 6 are the same as the composition 1.

Preparation Example 3

Soft Capsule

| Components | Amounts used (g) |
| --- | --- |
| Composition 1 | 100 |
| Tocopherol | 0.2 |

The components described above can be weighed respectively and homogeneously mixed, and formulated by being encapsulated into a soft capsule as the soft capsule preparation of which weight is 100 mg.

Preparation Example 4

Granule

| Components | Amounts used (g) |
| --- | --- |
| Composition 1 | 200 |
| Lactose | 450 |
| Corn starch | 300 |
| Hydroxypropylcellulose | 50 |
| Crystalline cellulose | 35 |

The components described above can be weighed respectively and homogeneously mixed, and formulated granule in the conventional method.

Preparation Example 5

Syrup

| Components | Amounts used (g) |
| --- | --- |
| Composition 1 | 2 |
| Saccharine | 0.6 |
| Sugar | 30 |

-continued

| Components | Amounts used (g) |
|---|---|
| Glycerin | 5 |
| Seasoning Agent | 0.1 |
| 96% ethanol | 10.4 |
| Purified water | Sufficient amounts for the final volume 100 mL |

The components described above can be weighed respectively; after sugar and saccharin are dissolved in 60 mL of distilled water for injection, glycerin and the composition 2 dissolved in ethanol and a solution of the seasoning agent were added. The purified water can be added to the mixture and adjusted the final volume is 100 mL to prepare a syrup for oral administration.

Preparation Example 6

Granule

| Components | Amounts used (g) |
|---|---|
| Composition 1 | 100 |
| Calcium silicate | 100 |

The components described above can be weighed respectively, and the composition 3 being adsorbed on calcium silicate and then form fine particles to formulate a powder preparation.

Accordingly, the pharmaceutical composition of the present invention is expected that it has wide range of applicability, and it is considered to be highly useful, for example, in the following application ways, particularly, in a variety of scene in which alveolar bone maintenance or promotion of alveolar bone formation is desired.

formation the following applications, particularly

According to the present invention, the pharmaceutical composition, the pharmaceutical preparation, health food, and the functional food comprising at least one selected from the group consisting of the present compounds (I) to (IVa), the glycosides thereof, the physiologically acceptable salts thereof, the hydrates thereof, and extracts comprising them is useful in the fields of pharmaceuticals and foods.

What is claimed is:

1. A method for increasing bone mass of a patient having a bone disease being associated with bone loss, comprising the step of administering to a bone disease patient a pharmaceutical preparation for increasing bone mass of a patient having a bone disease being associated with bone loss comprising a diarylheptanoid compound shown in the following formula (II):

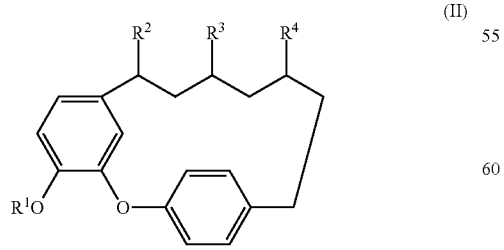

(II)

wherein in the formula (II), $R^1$ is selected from the group consisting of a hydrogen atom, alkyl group having carbon numbers 1 to 3, monosaccharide and disaccharide; and $R^2$, $R^3$ and $R^4$ are functional groups selected from the group consisting of a hydrogen atom, an oxygen atom, hydroxyl group, monosaccharide and disaccharide.

2. The method for increasing bone mass of a patient having bone disease being associated with loss of bone mass according to claim 1, wherein the dosage form of the pharmaceutical preparation is a sustained release dosage form.

3. The method for increasing bone mass of a patient having bone disease being associated with loss of bone mass according to claim 1, wherein the diarylheptanoid compound of formula (II) is one selected from the group consisting of the compounds shown in the following formulae (IIa) to (IIh):

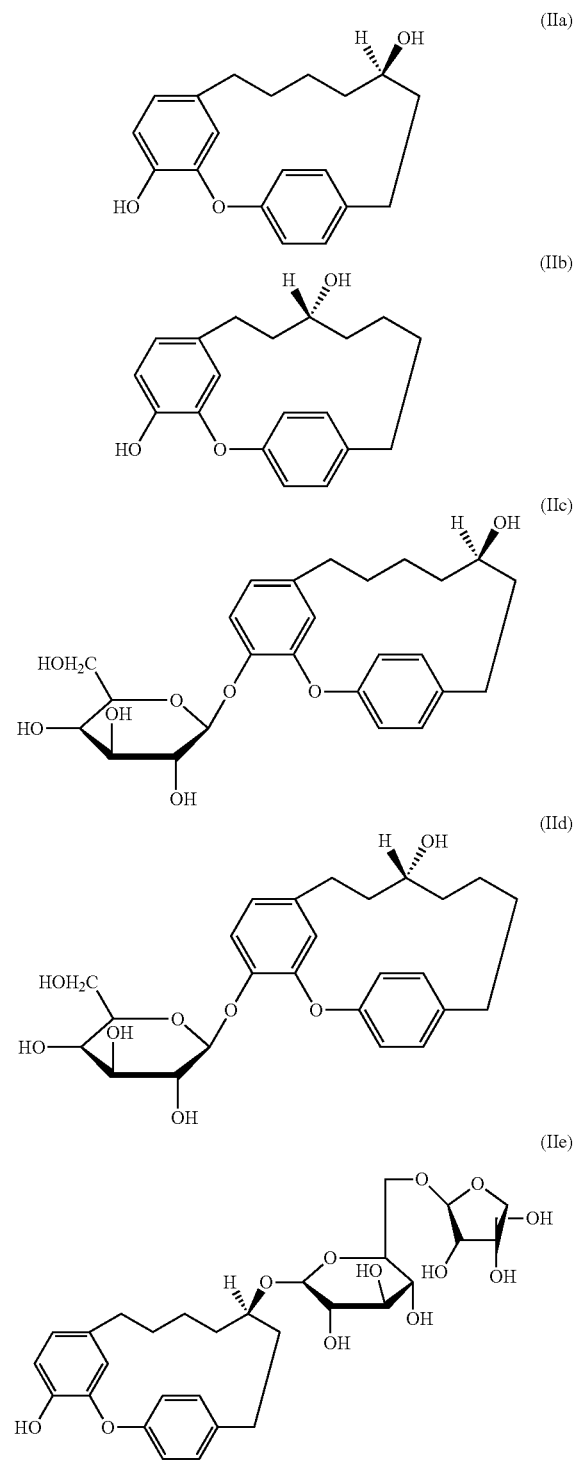

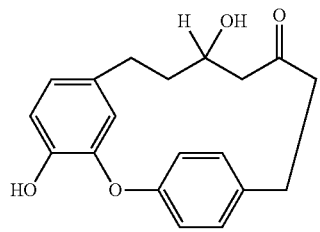
(IIf)

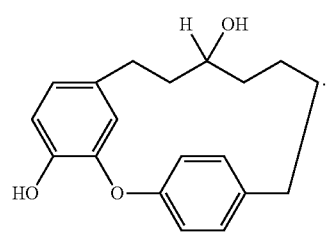
(IIh)

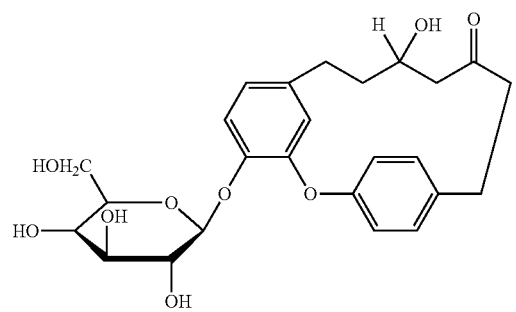
(IIg)

4. The method for increasing bone mass of a patient having bone disease being associated with loss of bone mass according to claim 1, wherein an amount of the diarylheptanoid compound contained in the pharmaceutical preparation is 0.1 to 100 mg per dose.

5. The method for increasing bone mass of a patient having bone disease being associated with loss of bone mass according to claim 1, wherein the pharmaceutical preparation is administered at a dosage of 1 mg/kg to 1,000 mg/kg of the diarylheptanoid compound.

* * * * *